United States Patent [19]

Elphick et al.

[11] Patent Number: 5,152,282
[45] Date of Patent: Oct. 6, 1992

[54] LIQUID-PROOF BARRIER MEANS FOR VARIOUS BODY AREAS

[76] Inventors: Kevin J. Elphick, 96 Mullaloo Drive, Kallaroo, Western Australia 6025; Ilene F. Watters, 1/197 Walter Road, Dianella, Western Australia 6062, both of Australia

[21] Appl. No.: 490,670
[22] PCT Filed: Sep. 12, 1987
[86] PCT No.: PCT/AU88/00356
§ 371 Date: Mar. 30, 1990
§ 102(e) Date: Mar. 30, 1991
[87] PCT Pub. No.: WO89/02259
PCT Pub. Date: Mar. 23, 1989

[30] Foreign Application Priority Data

Sep. 10, 1987 [AU] Australia .................. PI4272

[51] Int. Cl.⁵ ........................................ A61F 13/00
[52] U.S. Cl. ........................... 604/180; 602/54; 602/57; 602/58; 602/63; 602/901
[58] Field of Search ............ 128/82, 83, 187, 168

[56] References Cited

U.S. PATENT DOCUMENTS

| | | |
|---|---|---|
| 2,911,974 | 11/1959 | Spence . |
| 3,824,998 | 7/1974 | Snyder . |
| 4,178,924 | 12/1979 | Baxter . |
| 4,363,317 | 12/1982 | Broucek . |
| 4,523,586 | 6/1985 | Couri . |

FOREIGN PATENT DOCUMENTS

| | | |
|---|---|---|
| 4906985 | 6/1986 | Australia . |
| WO8501439 | 4/1985 | World Int. Prop. O. . |
| WO8707137 | 12/1987 | World Int. Prop. O. . |

Primary Examiner—Robert A. Hafer
Assistant Examiner—Kerry Owens
Attorney, Agent, or Firm—Stevens, Davis, Miller & Mosher

[57] ABSTRACT

An improved liquid proof barrier for medical applications having a substantially impervious flexible layer and a strip attached to or integral with the layer about its periphery. The strip has an adhesive backing and is relatively flexible and elastically extendable. The improved barrier serves to inhibit the passage of liquid into the area which it covers.

16 Claims, 3 Drawing Sheets

LIQUID-PROOF BARRIER MEANS FOR VARIOUS BODY AREAS

The present invention relates to an improved barrier means particularly envisaged for use in inhibiting the passage of liquid into an area. For example, the improved barrier means may typically be used to protect of parts of a persons body, such as parts of a persons body covered with a dressing, from becoming wet when showing or bathing. Also, the improved barrier means may be used on machinery having flexible bodies and the like requiring substantially liquid proofing for the flexible bodies or parts thereof.

FIELD OF THE INVENTION

Generally, when a person having medical dressings on parts of his/her body is to shower or bath, a substantially water impervious covering layer, such as of plastics materials, is placed over such dressings and attached to the body by sticking plasters. Usually, expensive hypo-allegenic sticking plasters. To attempt to obtain a substantially water (or liquid) proof covering several layers of sticking plaster are used.

It has been found that such arrangement tends to leak by becoming unstuck at places where the body bends. Also, the multiple layers do not intend to all be attached with the same tension and passage ways are created between the sticking plaster and the body and/or between layers of the sticking plaster.

If such covering layers do leak and the dressing becomes wet the dressing must be replaced so as not to inhibit healing of a wound covered by the dressing and/or to inhibit the spread of water born infection.

Such sticking plasters tend to be aggressive in sticking to the skin of a person and can disturb the healing of the wound during removal of the covering layer.

Also, it is difficult to commence removing the covering layer due to the nature of its adhesion to the person's body.

We have discovered that the problem with the previous technique of covering dressings as described above, is that the sticking plaster is virtually inelastic. So while the skin of the person is liable to bend and stretch with movement, the prior art covering layers are prone to not so bending and stretching at their attachment to the body due to the limitation of the sticking plasters used.

SUMMARY OF THE INVENTION

The present invention provides an improved barrier means which seeks to overcome the above mentioned problems. In accordance with one aspect of the present invention there is provided an improved non-reusable barrier means for a body part characterized in that it comprises a covering made from a substantially liquid impervious flexible material, the covering being in the form of either a bag with an open end or a tube with two or more open ends, and a liquid impervious strip either attached to or integral with a periphery of the or each open end such that the strip traverses the entire periphery for sealing the periphery to the body part, the strip having an adhesive backing which is non-aggressive and liquid impervious, the strip being relatively flexible and elastically extendable, the adhesive backing being disposed inwardly with respect to the periphery, a crease formable by manipulation of the strip, and an adhesive edge formable by sticking the adhesive backing onto itself from the crease toward the body part such that there is little or no mutual contact of the adhesive backing at the body part, the adhesive edge being disposable for sticking to an outside of the covering adjacent the periphery to finalise sealing of the or each open end to the body part and the adhesive edge extending along less than half the length of the periphery.

In accordance with another aspect of the present invention there is provided an improved non-reusable barrier means for a body part, characterised in that it comprises a layer made from a substantially liquid impervious flexible material, the layer being either relatively flat or slightly raised, and a liquid impervious strip either attached to or integral with a periphery of the layer such that the strip traverses the entire periphery for sealing the periphery to the body part, the strip having an adhesive backing which is non-aggresive and liquid impervious, the strip being relatively flexible and elastically extendible, a crease formed in one side of the layer by manipulation of the strip, and a tag created by the formation of the crease for enabling removal of the barrier means from the body part.

In accordance with another aspect of the present invention there is provided a method of applying a non-reusable barrier means to a body part, the barrier means having a covering made from, a substantially liquid impervious flexible material, the covering being in the form of either a bag with an open end or a tube with two or more open ends, and a liquid impervious strip either attached to or integral with a periphery of the or each open end, the strip having an adhesive backing and being relatively flexible and elastically extendible the method characterised in that it comprises the steps of placing the barrier means about the body part, sticking a portion of the strip to the body part, pulling the or each open end at the strip taut about the body part to form a crease, contacting a portion of the strip onto itself from the crease toward the body part such that there is little or no mutual contact of the adhesive backing of the body part forming an adhesive edge thereby, the adhesive edge extending along less than half the length of the periphery, and folding the adhesive edge onto a portion of the covering to finalise sealing of the or each open end to the body part.

In accordance with a further aspect of the present invention there is provided a method of applying a non-reusable barrier means to a body part, the barrier means having a layer made from a substantially liquid impervious flexible material, the layer being either relatively flat or slightly raised, and a liquid impervious strip either attached to or integral with a periphery of the layer, the strip having an adhesive backing and being relatively flexible and elastically extendible, the method characterised in that is comprises the steps of sticking an edge of the strip onto the body part, manipulating the layer to form a crease in one edge thereof, sticking the other edges of the layer onto the body part, propagating the crease into the layer thereby, sticking the strip in the crease onto itself to form a tag for removal of the barrier means and sticking the edge with the crease in it onto the body part.

The present invention will now be described with particular reference to use with humans but it is to be understood that it could be used for animals in general.

BRIEF DESCRIPTION OF THE DRAWINGS

The present invention will now be described by way of example with reference to the accompanying drawings in which.

DESCRIPTION OF THE INVENTION

Figure 1:
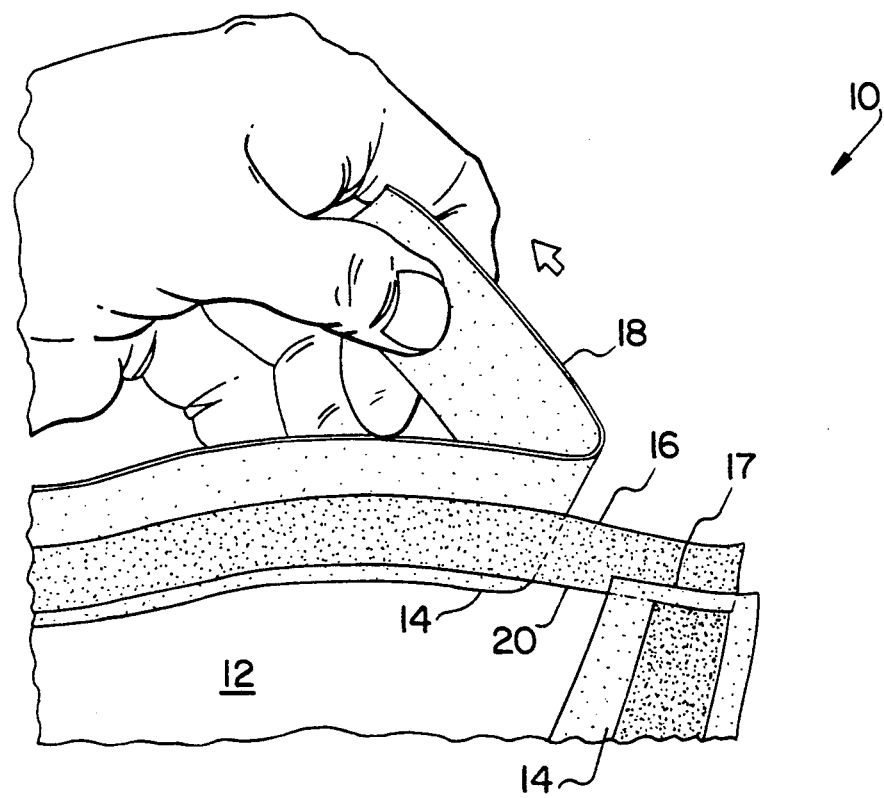
FIG. 1 is an enlarged front view of a barrier means according to the present invention.

In FIGS. 1 to 4, there is shown a barrier means 10 in accordance with the present invention. The barrier means 10 comprises a substantially liquid impervious flexible layer 12 having a periphery 14 particularly as shown in FIG. 1. Typically, the layer 12 is formed from a low density polyethylene plastics material or the like. The barrier means 10 also comprises strips 16 attached to the periphery 14 of the layer 12. The strip 16 have an adhesive backing 17, and are relatively flexible and elastically extendible. The adhesive backing 17 is preferably formed from non allergy adhesives to form a hypo-allegenic strip.

Preferably, the adhesive is a non-agressive adhesive to the extend that removal of the strip 16 from contact with a persons body causes little or not pain as regards adhesion to body hairs.

Prior art adhesives used in adhering layers to bodies tend to be quite aggressive and pain is usually associated with adhesion to body hairs when the strips are removed. This agressive adhesion can also lead to disruption of a healing wound.

The strips 16 preferably have an elasticity of greater than 1% elastic extension, typically in the range from 10% to 50% such as about 25%. The strips 16 may be made from elastic vinyl acetate (EVA) plastics material, rubber latex, vinyl or the like.

Preferably, the strips 16 are made from a substantially liquid proof material and particularly being water proof. The barrier means 10 also comprises strip covers 18 made of non stick or low stick plastics or silicone paper to protect the adhesive backing 17 prior to use. The strip covers 18 may readily be removed from the strips 16. Typically, there is one strip cover 18 for each side 19 of the barrier means 10. In the present embodiment there are typically four strip covers 18, although it is to be understood that there could be any number of strip covers 18.

The junction of the layer 12 and the strips 16 forms a hinge 20 at the periphery 14. The hinge 20 is created as a result of the differing flexibilities and elasticities of the layer 12 and the strips 16.

However, it is envisaged that in the event that a relatively elastic layer 12 is employed the adhesive backing 17 could be applied directly to and adjacent to the periphery 14 of the layer 12, thereby negating the need for a separate strips 16 to be attached to the periphery 14. It is envisaged that the layer 12 could be raised in parts and could be other than square.

Figure 2:
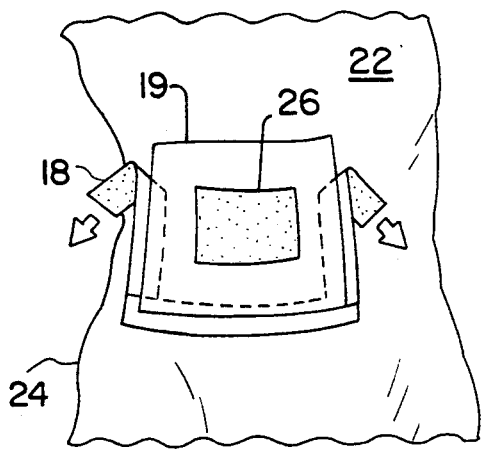
FIGS. 2 to 4 show a method of use of the barrier means of FIG. 1 according to a novel method of the present invention, and showing to a torso of a person.
Figure 3:
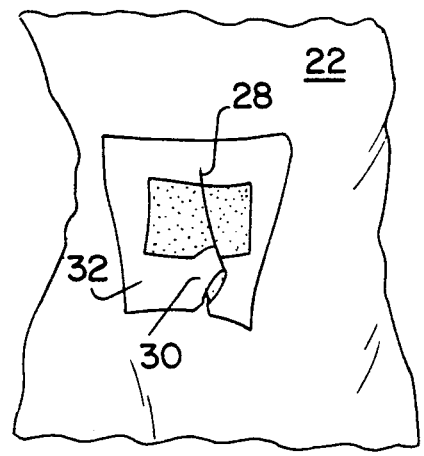
Figure 4:
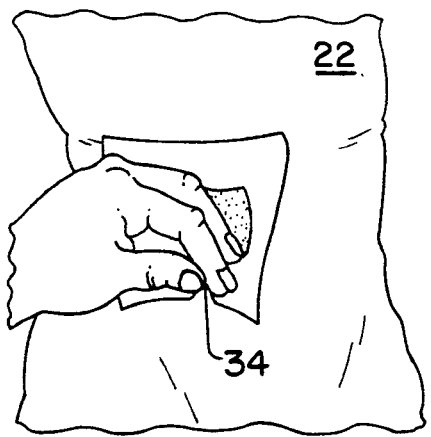

In use, the barrier means 10 of the present invention may be applied to a torso 22 of a person 24 to cover a dressing 26 as shown in FIGS. 2 to 4 to inhibit wetting of the dressing, such as during showering or bathing.

To apply the barrier means 10 one of the strip covers 18 is removed to reveal the adhesive backing 17 of one of the sides 19. That side 19 is then pressed onto the torso 22 to stick thereto above the dressing 26 as shown in FIG. 2.

The remainder of the strip covers 18 are then removed to reveal the remainder of the adhesive backings 17. The sides 19 adjacent the side 19 which is already adhered to the torso are next pushed toward the dressing to form a crease 28 in the layer 12 as shown in FIG. 3. The side 19 in which the crease 28 is formed is preferably lowermost on the torso 22 or other part of the person 24.

The sides 19 adjacent the side with the crease 28 in it are then pressed onto the torso 22 to adhere the same. The crease 28 creates a tapering in the layer 12 from the first mentioned side 19 to the side 19 having the crease 28 as shown in FIG. 3. This is advantageous in that liquid flowing down the torso 22 tends to leave the sides 19 between the first mentioned side 19 and the side 19 with the crease 28 and so reduces the likelihood to leakage of the barrier means 10.

The side 19 with the crease 28 is pressed onto the torso 22 and onto itself about the crease 28 to form a tag 30 as shown in FIG. 3.

The tag 30 forms a pocket 32 to allow the barrier means 10 to fit about a relatively thick dressing 28. It is to be noted that dressings can be as much as about 3 cms thick. Also, the tag 30 allows for relatively easy removal of the barrier means 10 once a substantially water resistant barrier is no longer required. Upon pulling the tag 30 the strip 16 peels off itself and off the torso 22 to form a relatively triangular space 34 as shown in FIG. 4. Further pulling increases the angle of peel between the strip 16 and the torso 22 and the side 19 of the barrier means 10 may relatively easily be removed from the torso 22.

The remainder of the barrier means 10 is removed by further pulling the tag 30 toward the first mentioned side 19. In FIGS. 5 to 9 there is shown another barrier means 50 according to another embodiment of the present invention, similar to the barrier means of FIGS. 1 to 4, and like numerals denote like parts.

The barrier means 50 comprises a bag 52 of similar construction to the layer 12 and having an open end 54 dimensioned to receive a limb 56 of the person 24. The barrier means 50 comprises a periphery 58 similar to the periphery 14. The strips 16, the adhesive backing 17 and the strip covers 18 are similarly applied to the periphery 58, and form a hinge 20. Typically, only one strip 16 and one strip cover 18 is required.

The barrier means 50 also comprises an adhesive tab 60 for use as described hereinafter.

In use, the barrier means 50 is applied to cover a dressing 26 on a limb 56 of a person 24 to inhibit wetting of the dressing 26 such as during showering and bathing.

Figure 6:
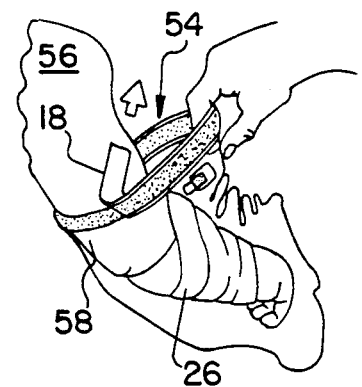
FIGS. 6 to 8 show a method of use of the barrier means of FIG. 5 according to a novel method of the present invention.

The open end 54 is placed about the linb 56 or similar part of the person 24. A portion of the strip cover 18, such as about one third in length, is peeled off the adhesive backing 17. The adhesive backing is contacted with the limb 56 as shown in FIG. 6.

The open end 54 is then made taunt, typically by gripping the open end 54 opposite the limb 56 to form a crease 62 and pulling the crease 62 in a direction substantially perpendicular to the limb 56. The crease 62 is at a free end of the open end 54.

Figure 5:
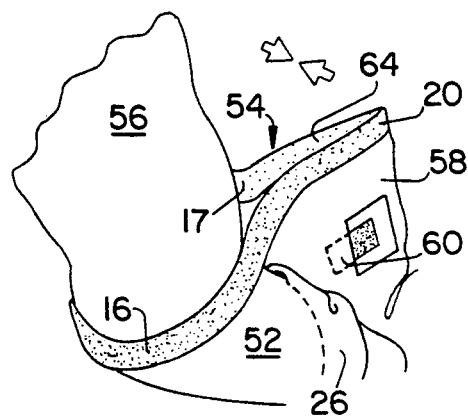
FIG. 5 is an enlarged view of a barrier means in accordance with another embodiment of the present invention shown attached to an arm of a person.
Figure 7:
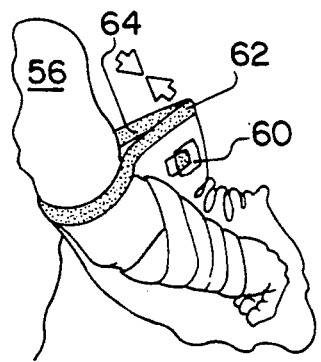
Figure 8:
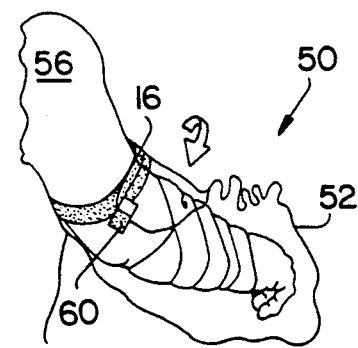

The remainder of the strip cover 18 is then removed and the adhesive backing 17 stuck onto itself from the crease 62 toward the limb 56 such that there is little or no mutual contact of the adhesive backing at the limb 56 such as shown in FIGS. 5 and 7. This forms an adhesive edge 64 which is then folded onto a portion of the bag 52 across the strip 16 as shown in FIG. 8.

That is two parts of the strip 16 are stuck diagonally together to create the adhesive edge 64. The adhesive edge 64 extends from adjacent the crease 62 and along less than half the perimeter of the open end 54.

Such method is employed so as to reduce the likelihood of a triangle forming between the limb 56 and the two parts of the strip 16, if total mutual adhesion was used. Also, such total mutual adhesion fails to create the edge 64. The tab 60 is then peeled off the bag 52 and used to stick the crease 62 to the bag 52 as shown in FIG. 8, to inhibit the edge 64 becoming unstuck.

Also, the adhesive edge 64 and the tab 60 may be tensioned to provide a tourniquet type effect in constricting the open end 54 about the limb 56.

Figure 9:
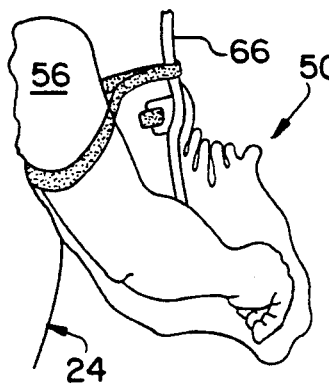
FIG. 9 shows use of the barrier device of FIG. 5 with an intravenous drip.

As shown in FIG. 9, an intravenous drip 66 may be passed into the bag 52, typically at the crease 62. The edge 64 and the tab 60 then serve to also secure the drip 66 to the limb 56 to immobilize same and to inhibit wetting of the limb 56 adjacent to a needle (not shown) connecting the drip 66 into the limb.

It is envisaged that the bag could be a tube, having two open ends 54 for use on limbs and/or torsos and the like of the person. Also, the tube could have more than two open ends, such as three open ends.

By the use of the barrier means 10 and 50 of the present invention, a more reliable barrier for dressings 26 occurs. Also, less adhesive tape is required with consequent reduction in cost. Further, the time taken to apply the barrier means 10 and 50 has been found to be less than the techniques of the prior art and may generally be carried out by the person who is wearing the dressing 26. Still further, the incidence of having to replace dressings 26 because they have become wet during showering or bathing is reduced. Still further, due to the use of relatively non aggressive adhesives disturbance of a healing wound is less likely.

Modifications and variations such as would be apparent to a skilled addressee are deemed within the scope of the present invention.

We claim:

1. An improved barrier means for location about a body part to inhibit ingress of liquid such as when wetting with water, the barrier means comprising:
   a covering formed from flexible, liquid impervious material, the covering having an open end dimensioned for receiving the body part; and,
   a strip formed from flexible, liquid impervious material, said strip extending in an integral and contiguous manner about the entire periphery of the open end for sealing the periphery to the body part, the strip having an adhesive backing located along its length and disposed for adhering the open end to the body part, the adhesive backing being liquid impervious, and the strip being elastically extendible for facilitating movement of the strip with movement of the body part while the strip is adhered to the body part by the adhesive backing;
   a crease located remote from the body part, the crease being formable by manipulation of the strip and adjacent periphery of the open end;
   an adhesive edge disposed between the crease and the body part, said adhesive edge formed by further manipulation of the strip and adjacent periphery of the open end so that a first part of the strip in the vicinity of the crease adheres to itself, a second part of the strip extending from one end of said first part to said body part adheres to the periphery and is orientated diagonally thereto, and a third part of the strip extending from an opposite end of said first part to said body part remains exposed to form said adhesive edge, the adhesive edge being disposed for adhering to an outside of the covering adjacent the periphery to overlie said second part of said strip and complete sealing of the open end to the body part.

2. An improved barrier means according to claim 1, also comprising an adhesive tab disposed for attaching the crease, adjacent the strip, to the covering.

3. An improved barrier means according to claim 1, in which the crease is capable of receiving and sealing against a tube for carrying fluids into the body part, such as an intravenous drip tube.

4. An improved barrier means according to claim 1, in which the adhesive backing is non-aggressive.

5. An improved barrier means according to claim 1, in which the covering is elastically extendible for elastically deforming with movement of the body part.

6. An improved barrier means according to claim 1, in which the covering is in the form of a bag designed to receive the body part.

7. An improved barrier means according to claim 1, in which the covering is in the form of a tube having two identical open ends, the open ends each being provided with an identical strip, the tube being designed to receive the body part extended through both of the open ends and the strips being disposed for sealing the periphery of the open ends to the body part.

8. An improved barrier means for location upon a body part to inhibit ingress of liquid such as during bathing, the barrier means comprising:
   a web formed from flexible, liquid impervious material shaped for attachment onto the body part;
   a strip formed from flexible, liquid impervious material, said strip extending in an integral and contiguous manner about the entire periphery of the web for sealing the periphery onto the body part, the strip having an adhesive backing located along its length and disposed for adhering the periphery onto the body part, the adhesive backing being liquid impervious, and the strip being elastically extendible for facilitating movement of the strip with movement of the body part while the strip is adhered onto the body part by the adhesive backing;
   a crease located in an edge of the web, the crease being formable by manipulation of the strip, and the crease acting as a tag for facilitating removal of the barrier means from the body part, wherein the formation of said crease creates a receptacle in the web for receiving a dressing attached onto the body part.

9. An improved barrier means according to claim 8, in which the web is elastically extendible for elastically deforming with movement of the body part.

10. An improved barrier means according to claim 8, in which the web is relatively non-elastically extendible and there is a hinge formed at the junction of the strip and the web, whereby, in use, the web is capable of hinged movement with respect to the strip.

11. A method of applying a barrier means, the barrier means comprising a covering which is flexible and substantially liquid impervious, the covering having an open end and a liquid impervious strip which is relatively flexible and elastically extendible and having an adhesive backing, the strip extending in an integral and contiguous manner about the entire periphery of the open end, the method comprising the steps of:

inserting the body part into the covering through the open end, adhering a portion of the strip to the body part to prevent rotation of said barrier means, pulling the open end of the covering taut about the body part to form a crease remote from the body part, contacting a portion of the covering onto itself from the crease towards the body part so that a first part of the strip in the vicinity of the crease adheres to itself, a second part of the strip extending from one end of said first part to said body part adheres to the periphery and is diagonally orientated thereto, and a third part of the strip extending from an opposite end of said first part to said body part remains exposed to form an adhesive edge, the adhesive edge extending along less than half the length of the periphery, and folding the adhesive edge onto a portion of the covering to overlie said second part of the strip and effect complete sealing of the open end to the body part.

12. A method according to claim 11, also comprising the step of elastically extending the strip by between 10% to 50% of its length prior to sealing the adhesive edge onto the covering for providing a tourniquet type effect for further sealing the open end onto the body part.

13. A method according to claim 11, further comprising the step of avoiding overlapping the strip at the juncture of the adhesive edge with the body part.

14. A method according to claim 11, further comprising the step of placing a tube in the crease for carrying fluids into the body part, such as an intravenous drip tube.

15. A method according to claim 11, further comprising the step of adhering the creases adjacent the strip to the covering with an adhesive tab.

16. A method of applying a barrier means to a body part, the barrier means comprising a web which is flexible and substantially liquid impervious, and a liquid impervious strip which is relatively flexible and elastically extendible and having an adhesive backing, the strip extending in an integral and continuous manner about the entire periphery of the web, comprising the steps of:

adhering a first edge of the strip onto the body part, manipulating the web to form a crease in a second edge opposite the first edge, propagating the crease into the web to form a receptacle to receive a dressing attached to the body part, adhering the other edges of the web onto the body part, adhering the strip in the vicinity of the crease onto itself to form a tag for removal of the barrier means and adhering the edge with the crease in it onto the body part to seal the web onto the body part over the dressing.

* * * * *